United States Patent [19]

Henze

[11] 4,431,626
[45] Feb. 14, 1984

[54] TC-99M LABELED CARRIER FOR IMAGING

[75] Inventor: Eberhard Henze, Santa Monica, Calif.

[73] Assignee: The Regents of the University of California, Berkeley, Calif.

[21] Appl. No.: 268,319

[22] Filed: May 27, 1981

[51] Int. Cl.³ .................... A61K 43/00; A61K 49/00
[52] U.S. Cl. ......................................... 424/1.1; 424/9
[58] Field of Search ................................ 424/1, 9, 1.5

[56] References Cited

U.S. PATENT DOCUMENTS

| 2,653,931 | 9/1953 | Isbell | 260/209 |
|---|---|---|---|
| 2,677,645 | 5/1954 | Allen | 424/7 |
| 3,758,678 | 9/1973 | Lindsay et al. | 424/1 |
| 3,852,413 | 12/1974 | Cammarata | 424/9 |
| 4,002,730 | 1/1977 | Hartman et al. | 424/1 |
| 4,106,488 | 8/1978 | Gordon | 424/1 |
| 4,124,705 | 11/1978 | Rothman et al. | 424/4 X |
| 4,126,669 | 11/1978 | Rothman et al. | 424/1 |
| 4,303,636 | 12/1981 | Gordon | 424/1 |
| 4,359,453 | 11/1982 | Gordon | 424/1 |

OTHER PUBLICATIONS

Steigman et al., J. Label. Comp. Radiopharm., 16: 83–85.
Johnson et al., J. Biol. Nucl. Med., 11: 103–106, (1967).
Hamilton et al., Experientia, 34: 582–583, (1978).

Primary Examiner—Christine M. Nucker
Attorney, Agent, or Firm—Bertram I. Rowland

[57] ABSTRACT

Novel radionuclide imaging agents, having particular application for lymphangiography are provided by non-covalently binding Tc-99m to a pharmaceutically acceptable cross-linked polysaccharide. Upon injection of the Tc-99m labeled polysaccharide into the blood stream, optimum contrast can be obtained within one hour.

7 Claims, No Drawings

TC-99M LABELED CARRIER FOR IMAGING

The Government has rights in this invention pursuant to Contract No. DE-AMO3-76-SF00012 by the U.S. Department of Energy.

BACKGROUND OF THE INVENTION

1. Field of the Invention

Lymphangiography is an important tool in diagnostic radiology for examination of a variety of diseases, i.e. lymphedema, lymphoma and carcinoma metastatic disease. However, lymphangiography requires time consuming surgical preparation of lymph vessels, injection of iodine containing contrast medium and considerable x-ray exposure of the patient. On the other hand, no radiolabeled compounds are available to date that allow radionuclide lymphangiography. Tc-99m HIDA and Tc-99m sulfur colloid are inadequate, since they fail to trace the lymphatic system satisfactorily due to label instability and very slow migration of the rather small molecule.

2. Description of the Prior Art

Steckel et al, Am. Journal of Roentgenology, Radium Therapy and Nuclear Medicine 124, 600–609 (1975) describes the use of albumin as a Tc-99m carrier for imaging.

SUMMARY OF THE INVENTION

Technetium-99m labeled cross-linked polysaccharides are employed as a radiopharmaceutical for lymphangiography and gated blood pool imaging. The product is prepared in conventional ways by in situ reduction of Tc-99m in the presence of the polysaccharide, whereby the polysaccharide becomes labeled with the Tc-99m. Conveniently, the polysaccharide is combined with a sufficient amount of an effective reducing agent, so that the Tc-99m reagent can be rapidly prepared immediately prior to use.

DESCRIPTION OF THE SPECIFIC EMBODIMENTS

Tc-99m labeled polysaccharides are provided of a range of molecular weights, by reducing Tc-99m pertechnetate with an appropriate reducing agent in the presence of a polysaccharide. The reduced pertechnetate binds to the polysaccharide to provide a stable link with the polysaccharide. Conveniently, the reducing agent and polysaccharide may be preprepared for combination with the Tc-99m pertechnetate to rapidly produce the radiopharmaceutical prior to use.

Pertechnetate has a short half life, so that it is obtained by the decay of Mo-99 and the extraction and purification of the pertechnetate from the molybdenum solution, being normally obtained as a dilute saline solution. It may be prepared at the site of use, but is usually prepared at a central site and rapidly delivered to the location where the imaging agent is required. Once delivered, the pertechnetate is reduced to Tc-99m and formulated in a variety of ways depending upon the organ or organs to be imaged.

In accordance with the subject invention, the pertechnetate is combined with a polysaccharide of at least about 25,000 daltons in the presence of a pharmaceutically acceptable reducing agent which results in a pharmaceutically acceptable product. The in situ reduced Tc-99m stably binds to the polysaccharide, which may then be purified in conventional ways and used as a blood pool imaging agent for gated radionuclide angiography.

The polysaccharide which is employed will generally be a polyglucoside of at least about 25,000 molecular weight, pharmaceutically acceptable, and relatively non-degradable in the mammalian host, normally a human. The non-biodegradability may be due to crosslinking, the nature of the saccharide or linking group, combinations of these or the like. Of particular interest is dextran and hetastarch of from about 25,000 to 5,000,000 molecular weight, preferably of from about 40,000 to 2,000,000 molecular weight and more preferably from about 250,000 to 750,000 molecular weight.

The reducing agent is any convenient pharmaceutically acceptable reducing agent which will allow for reduction of the pertechnetate to Tc-99m without interfering with the binding of the Tc-99m to the polysaccharide. Because of the low concentration of the reducing agent and the small amount introduced into the host, relatively toxic compounds can be tolerated, which are non-toxic at the level employed. Both the reductant and the product of the reductant are pharmaceutically acceptable or relatively easily removed, preferably pharmaceutically acceptable. A particularly useful reagent is a stannous salt with a pharmaceutically acceptable anion e.g. chloride. Conveniently, the reducing agent and polysaccharide may be preprepared to provide a reagent which may be directly combined with the pertechnetate, the reaction allowed to proceed for a few minutes to ensure completion, and then followed by use.

The weight ratio of reductant to polysaccharide is not significant and will vary with the reductant and the polysaccharide, generally ranging from about 0.2–5:1. With stannous chloride and dextran, the weight ratio will generally be about 1–2:1. The solution will normally be acidic, generally having a low pH, conveniently in the range of about 1–4. The reagent solution will normally be free of oxygen and filtered prior to combination with the pertechnetate.

The reagent solution can be stored for long periods of time at temperatures under 10° C., normally above freezing and up to about 4° C., e.g. 2°–4° C. The ratio of Tc-99m to dextran based on mCi will generally be about 1 mCi per 0.01 to 1 mg, usually about 0.05 to 0.5 mg of dextran. The concentration of dextran in the solution will generally be from about 5 to 20%, more usually from about 7 to 15%, preferably about 10% by weight. The solution will be a pharmaceutically acceptable vehicle, conveniently a saline solution.

Administration will normally be parenteral particularly by injection, e.g. subcutaneously or intravenously. Normally sufficient amount of the Tc-99m will be introduced to provide sufficient contrast for the imaging of the organ of interest. Usually, for lymphangiography the dosage will be about 0.5 to 1.5 mCi, more usually about 1 mCi, while the dosage for gated pool blood imaging will be about 20 fold greater, usually in the range of about 15 to 25 mCi per injection.

In order to demonstrate the subject invention, reagents were prepared with a variety of dextrans of different molecular weight: 40,000 daltons (D×40); 500,000 daltons (D×500); and 2,000,000 daltons (D×2000).

Stannous-dextran reagents were prepared by dissolving 1.5 mg of stannous chloride in 50 ml of conc.HCl, followed by the addition with vigorous mixing of 10 ml of deoxygenated aqueous saline 10 weight percent dextran solution. The dextran solution is deoxygenated by bubbling nitrogen through the solution at 50 ml/min for at least about one hour. Under aseptic conditions, 1 ml aliquots of the stannous-dextran reagent solution is dispensed through a millipore membrane filter into 5 ml vials, which are then stoppered and sealed under a nitrogen atmosphere. The sterile reagent can be stored at 2°-4° C. until use. Pertechnetate Tc-99m in a saline solution providing about a 20 mCi dose of Tc-99m is combined with 2-3 ml of the dextran reagent and the mixture allowed to stand for about 5 min. at room temperature before injection. Paper chromatographic analysis using 0.9% NaCl and separate analysis using 2-butanone verified a labeling yield in excess of 98%.

The compositions where then used in seven mongrel dogs to determine body distribution kinetics and suitability for blood pool imaging. The tin-dextran reagent preparations (1 ml 10 weight percent dextran in saline) were stored for weeks and Tc-99m pertechnetate added minutes prior to injection. Tc-99m remained totally bound to dextran in vivo: there was no evidence for free Tc-99m in blood, urine, thyroid, stomach or salivary glands. Activity was excreted through the kidney only in the form of Tc-99m dextran reagent.

Whole body distribution showed appreciable activity only in the circulatory system, the liver and urinary bladder. The organ activity time course depended upon the molecular weight of dextran used. TcD×40 showed a high initial urinary excretion rate, while TcD×2000 was initially accumulated in the liver and then excreted, which caused a fast decline in blood activity. Blood pool activity was optimal with TcD×500 with a clearance half time of about two hours. With this agent optimum added blood pool imaging could be obtained within one hour, with a target to background ratio of 9.1 decreasing to 7.3 within 60 minutes after injection. The corresponding ratios for in vitro labeled red blood cells as an optimum reference were 9.9 and 9.1.

In another test employing 15.0 mCi of the reagent in dogs, five minutes after injection, about 20% of the total activity was in the liver and 20% in the blood pool in the heart, while the activity in the urinary bladder was negligible. After 150 minutes, there was an increase uptake of the urinary bladder (about 30%), while the liver activity remained relatively constant. The blood clearance half life was about one hour using D×500.

In another test employing 1.0 mCi for lymphangiography, radionuclide angiograms obtained after subcutaneous interdigital injections (hind limb) showed excellent contrast of lymph vessels of the hind limb, as well as well visualized lymph nodes of the inguinal and pelvic area.

It is evident from the above results, that Tc-99m dextran is an agent highly suitable for gated blood pool imaging and lymphangiography. Its advantages are simple chemical preparation and technical handling as well as extremely stable labeling. In addition, it provides high contrast gated blood pool imaging for sufficiently long periods of time.

Although the foregoing invention has been described in some detail by way of illustration and example for purposes of clarity of understanding, it will be obvious that certain changes and modifications may be practiced within the scope of the appended claims.

I claim:

1. A reagent useful for the reduction of pertechnetate comprising stannous chloride and a pharmaceutically acceptable water soluble dextran of at least about 25,000 molecular weight in a pharmaceutically acceptable aqueous vehicle.

2. A composition according to claim 1, wherein said dextran of from about 25,000 to 5,000,000 molecular weight present in an amount of from about 5 to 20 weight percent and said stannous chloride is present in from about 5 to 25 weight percent.

3. A composition according to claim 2, wherein the weight ratio of stannous chloride to dextran is 0.2-5:1 and said vehicle is a pharmaceutically acceptable saline solution.

4. A radioimaging reagent comprising Tc-99m bound to a water soluble dextran of at least about 25,000 molecular weight by in situ reduction of pertechnetate in the presence of said dextran,
   wherein said in situ reduction comprises:
   contacting said pertechnetate with stannous chloride at a weight ratio of about 1-2:1 and at a pH in the range of about 1-4.

5. An imaging reagent according to claim 4, wherein said dextran of from about 40,000 to 2,000,000 daltons.

6. A method for radioimaging in a host, which comprises injecting Tc-99m bound to a water soluble dextran of at least about 25,000 molecular weight by in situ reduction of pertechnetate in the presence of said dextran, in a pharmaceutically acceptable vehicle in an amount sufficient to provide imaging contrast for an organ of interest,
   wherein said in situ reduction comprises:
   combining stannous chloride with said pertechnetate at a weight ratio of about 1-2:1 of stannous chloride to dextran at a pH in the range from about 1-4.

7. A method according to claim 6, wherein said dextran is from about 40,000 to 2,000,000 molecular weight.

* * * * *